United States Patent [19]

Diehl et al.

[11] Patent Number: 5,266,394
[45] Date of Patent: Nov. 30, 1993

[54] DISPOSABLE ARTICLES OF MANUFACTURE CONTAINING POLYSTYRENE-POLYISOPRENE-POLYSTYRENE BLOCK COPOLYMERS

[75] Inventors: Charles F. Diehl; Michael O. Myers; Jean M. Tancrede, all of Baton Rouge, La.

[73] Assignees: The Dow Chemical Company, Midland, Mich.; Exxon Chemical Patents, Inc., Linden, N.J.

[21] Appl. No.: 925,385

[22] Filed: Aug. 4, 1992

Related U.S. Application Data

[62] Division of Ser. No. 393,545, Aug. 11, 1989, Pat. No. 5,143,968.

[51] Int. Cl.$^5$ .............................. B32B 27/04
[52] U.S. Cl. ................................ 428/261; 428/286; 428/349; 428/355
[58] Field of Search ........... 525/98, 314; 524/534; 428/349, 355, 261, 286

[56] References Cited

U.S. PATENT DOCUMENTS

| | | | |
|---|---|---|---|
| 3,149,182 | 9/1964 | Porter | 260/879 |
| 3,231,635 | 1/1966 | Holden et al. | 260/880 |
| 3,238,173 | 1/1966 | Bailey et al. | 260/29.7 |
| 3,239,478 | 3/1966 | Harlan, Jr. | 260/27 |
| 3,427,269 | 2/1969 | Davis et al. | 260/27 |
| 3,595,942 | 7/1971 | Wald | 525/98 |
| 3,614,836 | 10/1971 | Snyder et al. | 36/2.5 |
| 3,700,633 | 10/1972 | Wald et al. | 360/880 B |
| 3,736,281 | 5/1973 | Russel | 260/27 R |
| 3,784,587 | 1/1974 | Chambers | 260/876 B |
| 3,880,953 | 4/1975 | Downey | 360/876 B |
| 3,932,329 | 1/1976 | Lakshmanan | 260/27 R |
| 3,949,020 | 4/1976 | Prudence | 260/879 |
| 4,096,203 | 6/1978 | St. Clair | 260/876 B |
| 4,117,037 | 9/1978 | Himes | 260/880 B |
| 4,163,077 | 7/1979 | Antonsen et al. | 428/355 |
| 4,163,764 | 8/1979 | Nash | 525/2 |
| 4,172,860 | 10/1979 | Feeney et al. | 525/97 |
| 4,205,679 | 6/1980 | Repke et al. | 128/287 |
| 4,212,910 | 7/1980 | Taylor et al. | 428/35 |

(List continued on next page.)

FOREIGN PATENT DOCUMENTS

| | | |
|---|---|---|
| 0306232A2 | 8/1989 | European Pat. Off. . |
| 0333936A1 | 9/1989 | European Pat. Off. . |
| 0362850A2 | 4/1990 | European Pat. Off. . |
| 0451919A2 | 10/1991 | European Pat. Off. . |
| 0525251A1 | 2/1993 | European Pat. Off. . |
| 0525905A1 | 2/1993 | European Pat. Off. . |
| 1594267 | 3/1967 | Fed. Rep. of Germany . |
| 2942128 | 10/1979 | Fed. Rep. of Germany . |
| 56090849 | 12/1979 | Japan . |
| 58089672 | 11/1981 | Japan . |
| 61120732 | 11/1984 | Japan . |
| 1221244 | 11/1970 | United Kingdom . |
| 1447419 | 8/1976 | United Kingdom . |
| 1592358 | 7/1981 | United Kingdom . |

*Primary Examiner*—Jenna L. Davis
*Attorney, Agent, or Firm*—Pravel, Hewitt, Kimball & Krieger

[57] ABSTRACT

Polystyrene-polyisoprene-polystyrene block copolymers, hot-melt adhesive compositions constituted of polystyrene-polyisoprene-polystyrene block copolymers, and articles of manufacture produced therefrom. These copolymers possess blocks of high average molecular weight polystyrene (12,000 to 20,000) and low overall average molecular weight (60,000 to 110,000) such that when blended in requisite proportions with a compatible tackifier resin, preferably also a secondary tackifying resin or plasticizing oil, and stabilizer, superior hot-melt adhesive compositions can be formed. The hot-melt adhesive compositions possess, inter alia, superior heat resistance, superior static time to failure with low viscosity, good peel adhesion, good tack, and high ability to bond to a polyethylene or polypropylene substrate at temperatures below that which may damage the substrate.

29 Claims, No Drawings

U.S. PATENT DOCUMENTS

| | | | |
|---|---|---|---|
| 4,294,936 | 10/1981 | Korpman | 525/93 |
| 4,411,954 | 10/1983 | Butch, III et al. | 428/343 |
| 4,419,494 | 12/1983 | Puletti et al. | 525/95 |
| 4,526,577 | 7/1985 | Schmidt, Jr. et al. | 604/366 |
| 4,540,415 | 9/1985 | Korpman | 604/390 |
| 4,578,302 | 3/1986 | Schmidt, Jr. et al. | 428/110 |
| 4,660,858 | 4/1987 | Flanagan | 281/21 R |
| 4,699,938 | 10/1987 | Minamizaki et al. | 524/271 |
| 4,725,641 | 2/1988 | Comert et al. | 524/499 |
| 4,785,043 | 11/1988 | Kawai et al. | 524/272 |
| 4,985,499 | 1/1991 | Nishikawa et al. | 525/89 |
| 4,997,709 | 5/1991 | Huddleston et al. | 428/344 |
| 5,019,071 | 5/1991 | Bany et al. | 604/389 |
| 5,028,646 | 7/1991 | Miller et al. | 524/77 |
| 5,057,571 | 10/1991 | Malcolm et al. | 524/505 |
| 5,118,762 | 6/1992 | Chin | 525/314 |
| 5,149,741 | 9/1992 | Alper et al. | 525/95 |

DISPOSABLE ARTICLES OF MANUFACTURE CONTAINING POLYSTYRENE-POLYISOPRENE-POLYSTYRENE BLOCK COPOLYMERS

This is a division of application Ser. No. 07/393,545 filed Aug. 11, 1989 now U.S. Pat. No. 5,143,968.

FIELD OF THE INVENTION

This invention relates to polystyrene-polyisoprene-polystyrene block copolymers, hot-melt adhesive compositions, and articles formed or constructed therefrom. In particular, it relates to polystyrene-polyisoprene-polystyrene block copolymers, and to improved hot-melt adhesive compositions formed from polystyrene-polyisoprene-polystyrene block copolymers, especially of a type useful in the assembly of disposable articles, particularly disposable articles wherein the hot-melt adhesive composition is employed in the construction to bond a polyethylene or polypropylene substrate to a tissue, non-woven fabric or absorbent fluff.

BACKGROUND

It is known to prepare hot-melt adhesive compositions from polystyrene-polyisoprene-polystyrene and polystyrene-polybutadiene-polystyrene block copolymers. There are numerous uses for hot-melt adhesives, but whereas one hot-melt adhesive may be useful in a given application, it may be unsuitable in another. For example, one particular hot-melt adhesive might be excellent for bonding together paper, or cardboard, but will not form acceptable bonds between certain rubbers, or metals. Moreover, some uses require bonding between substrates formed of different materials, and a given hot-melt adhesive may bond one type of substrate but not the other. Furthermore, it may be necessary that the hot-melt adhesive be applied at relatively low temperatures to avoid damage to one or the other of the substrates, or the bond must be flexible and provide adhesive elongation. Certain products, notably disposable articles, for example multi-line products, e.g., disposable diapers, sanitary napkins, bed pads, etc., are exemplary of articles of manufacture which require the use of hot-melt adhesive having such characteristics. Other articles of manufacture requiring the use of hot-melt adhesives include such operations as magazine and book binding, and elastic gluing operations generally.

In the construction of disposable diapers, sanitary napkins, and bed pads, e.g., hot-melt adhesives capable of bonding a non-woven moisture absorbent fabric, or moisture absorbent fluffy material, usually in layers, is applied as a continuous or discontinuous film to a substrate to bond said non-woven fabric or fluffy material thereto. In the construction of multi-line products via present techniques, e.g., in the construction of disposable diapers, a non-woven fabric, or absorbent fluffy material is generally bonded to an inner ply of a soft surfaced material, or tissue, which contacts the wearer's skin. An outer ply of moisture impervious material is adhered thereto via the use of a hot-melt adhesive to minimize moisture, or liquid strike-through. Whereas the adhesive can be sprayed, brushed or otherwise applied upon the surface of a substrate as a continuous or discontinuous film, it has become the practice to apply the adhesive as fine lines across the face of a substrate, or as a multi-dot pattern having a large number of adhesive droplets. As a result, these types of construction are generally termed "multi-line" constructions, and the products as "multi-line" products. The hot-melt adhesives used in the production of multi-line products must possess certain adhesive qualities not commonly shared by all adhesives.

In general, e.g., disposable diapers are constituted of a fluid impervious polyethylene, or polypropylene outer sheet and an inner moisture absorbent sheet covered by an inner lining of non-woven tissue. Hot-melt adhesives are applied in the form of fine parallel longitudinal strips to bond the layers together, and hence must possess sufficient adhesive and cohesive strength to provide high bond strength values so that when subjected to stress the constructions cannot be easily separated. It is also necessary that the adhesives withstand high mixing and application temperatures without thermal degradation and loss of adhesive properties, as well as good heat and oxidation resistance on aging. Good adhesive performance is required at elevated temperatures since the disposable articles are worn at body temperature, and also exposed to elevated temperatures during warehousing and shipping. The hot-melt adhesive must have low adhesive viscosity so that it can be applied at low temperature in order to avoid distortion of the polyethylene or polypropylene substrates to which it is applied. Quite obviously, all hot-melt adhesives do not possess these, and other useful properties to the same degree, or even to as high degree as would be desired; even those presently commercially used for multi-line constructions. There thus remains a need for improved hot-melt adhesive compositions useful in the assembly of multi-line constructions, and disposable articles of multi-line construction formed from improved hot-melt adhesive compositions. There likewise exists a need for hot-melt adhesives useful in magazine and book binding, and elastic gluing operations generally.

OBJECTS

It is, accordingly, a primary objective of this invention to fulfill these needs, and others.

A particular object of this invention is to provide novel polystyrene-polyisoprene-polystyrene block copolymers, and improved hot-melt adhesive compositions particularly useful in the assembly of disposable articles of manufacture, particularly disposable articles of multi-line construction.

A further, and more particular object is to provide hot-melt adhesive compositions which have superior heat resistance, superior static time to failure with low viscosity, good peel adhesion, and good tack and high ability to bond to a polyethylene or polypropylene substrate at temperature below that which would be injurious to the substrate.

A further, and yet more specific object is to provide disposable articles, particularly disposable articles of multi-line construction, wherein a polyethylene or polypropylene substrate is bonded to a tissue, or non-woven polyethylene or polypropylene substrate, or both, via the use of said improved hot-melt adhesive compositions.

THE INVENTION

These objects and others are achieved pursuant to the practice of this invention, embodying a novel polystyrene-polyisoprene-polystyrene block copolymer, and a novel hot-melt adhesive composition comprising said novel copolymer, compatible primary tackifier resin, preferably also a secondary tackifier resin or plasticizing oil, and stabilizer. The hot-melt adhesive composition is, in particular, comprised of said polystyrene-polyisoprene-polystyrene block copolymers the polystyrene blocks of which are sufficiently high average molecular weight to provide, inter alia, when blended in the requisite proportions with a compatible tackifier resin, preferably also a secondary tackifier resin or plasticizing oil, and stabilizer, high shear holding power and shear adhesion failure temperature, and a low overall molecular weight sufficient to provide low viscosity.

The novel polystyrene-polyisoprene-polystyrene block copolymer is characterized by any of the formulas:

$$B\text{—}(AB)_n \quad (1)$$

where n is 2, or greater than 2:

$$A\text{—}(BA)_n \quad (2)$$

where n is 1, or greater than 1: or $$(AB)_n \quad (3)$$

where n is 2, or greater than 2:
wherein, in any of formulas (1), (2) or (3), A is a polystyrene block having an average molecular weight ranging from about 12,000 to about 20,000, preferably from about 14,000 to about 19,000, B is a polyisoprene block having an average molecular weight ranging from about 30,000 to about 70,000, preferably from about 35,000 to about 60,000, the overall molecular weight of the block copolymer ranges from about 60,000 to about 110,000, preferably from about 70,000 to about 95,000, and the polystyrene block A components are present in an amount of at least about 27 parts to about 50 parts, preferably from about 35 parts to about 45 parts, per 100 parts by weight of the block copolymer. The A-B-A block copolymer of this invention can thus be a triblock or multi-block copolymer, and it is characterized by the presence of a B block, or polyisoprene block, located between two polystyrene blocks, or A blocks, which may or may not be terminal end blocks. The A-B-A triblock copolymer is preferred.

The hot-melt adhesive composition is, in particular, comprised of from about 15 percent to about 35 percent, preferably from about 20 percent to about 30 percent, based on the weight of the hot-melt adhesive composition, of said A-B-A block copolymer wherein the B component is polyisoprene having an average molecular weight ranging from about 30,000 to about 70,000, preferably from about 35,000 to about 60,000, the A component is polystyrene having an average molecular weight ranging from about 12,000 to about 20,000, preferably from about 14,000 to about 19,000, the overall molecular weight of the block copolymer ranges from about 60,000 to about 110,000, preferably from about 70,000 to about 95,000, and wherein the A component is present in an amount of at least about 27 parts up to about 50 parts, preferably from about 35 parts to about 45 parts, per 100 parts by weight of the block copolymer; from about 45 percent to about 70 percent, preferably from about 50 percent to about 60 percent, based on the weight of the hot-melt adhesive composition, of a compatible primary tackifying resin; from 0 percent to about 30 percent, preferably from about 5 percent to about 20 percent, of a plasticizing oil, or secondary tackifying resin, or both, based on the weight of the hot-melt adhesive composition; and from about 0.1 percent to about 2 percent, preferably from about 0.5 percent to about 1.5 percent of a stabilizer, based on the weight of the hot-melt adhesive composition.

These hot-melt adhesive compositions, constituted of an A-B-A block copolymer of intermediate to relatively high styrene content and overall low molecular weight to which the primary tackifying resin, the secondary tackifying resin or plasticizing oil, and stabilizer have been added, have been found to possess properties which are admirably suitable for the construction of disposable articles, particularly disposable articles of multi-line construction wherein the adhesive is applied as fine parallel longitudinal strips, or as a multi-dot pattern of adhesive droplets, to bond together a moisture impervious outer polyethylene or polypropylene sheet and an inner moisture absorbent sheet, or tissue, as used in diaper constructions. These adhesive compositions, with the addition of other materials, are also useful for magazine and book lining, or book binding, or as elastic glues generally. These hot-melt adhesive compositions can be melted, and maintained under a blanketing nitrogen atmosphere, at relatively low to high temperatures without thermal degradation. The compositions can be applied in fluid form to polyethylene and polypropylene substrates as continuous or discontinuous films, suitably as fine lines or as patterns of multi-dots, without any risk of damage to the polyethylene or polypropylene substrate. These hot-melt adhesive compositions have also been found to serve a construction function in binding together an outer sheet, or wrapper overlapped with an absorbent pad as required in the construction of sanitary napkins. The hot-melt adhesive composition applied as a fluid permeates the overlapped area to bind and seal the absorbent pad inside the outer sheet which serves as a wrapper.

The primary tackifying resins useful in the practice of this invention include hydrocarbon resins, synthetic polyterpenes, rosin esters and natural terpenes which are semi-solid or solid at ambient temperas, and soften or become liquid at temperatures ranging generally from about 70° C. to about 135° C., preferably from about 85° C. to about 120° C. Exemplary of the primary tackifying resins are compatible resins such as (1) natural and modified rosins such, for example, as gum rosin, wood rosin, tall oil rosin, distilled rosin, hydrogenated rosin, dimerized rosin, and polymerized rosin; (2) glycerol and pentaerythritol esters of natural and modified rosins, such, for example, as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g., styrene/terpene and alpha methyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicylic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol: (6) aliphatic petroleum hydrocarbon resins having a Ball and Ring softening point of from about 70° to 135° C.; the latter resins resulting from the polymerization of monomers consisting primarily of olefins and diolefins; also included are the hydrogenated aliphatic petroleum hydrocarbon resins; (7) aromatic petroleum hydrocarbon resins, and mixed aromatic and aliphatic paraffin hydrocarbon resins, and the hydrogenated derivatives thereof; (8) aromatic modified alicyclic petroleum hydrocarbon resins and the hydrogenated derivities thereof; and (9) alicyclic petroleum hydrocarbon resins and the hydrogenated derivatives thereof. The preferred primary tackifying resins for use in the practice of this invention are represented by sub-paragraphs (1), (3) and (7), supra. Suitable secondary tackifying resins are those named species wherein the resin is a liquid at ambient temperature.

Various plasticizing oils are useful in the practice of this invention. The plasticizing oil can be used in place of or in combination with the secondary tackifier to reduce viscosity and improve tack properties. Plasticizing oils which have been found useful include olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternately, the oil may be totally non-aromatic. The oligomers may be polypropylenes, polybutenes, hydrogenated polyisoprene, hydrogenated polybutadiene, polypiperylene and copolymers of piperylene and isoprene, or the like having average molecular weights between about 350 and about 10,000. Vegetable and animal oils include glyceryl esters of the usual fatty acids and polymerization products thereof.

The stabilizer, or antioxidant, used in accordance with the practice of this invention includes high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris (3,5-di-tert-butyl-4-hydroxybenzyl) benzene; pentaerythrityl tetrakis-3 (3,5-di-tert-butyl-4-hydroxyphenyl) propionate; n-octadecyl-3 3,5-di-tert-butyl-4-hydroxyphenyl)-propionate; 4,4'-methylenbis (2,6-tert-butylphenol); 4,4'-thiobis (6-tert-butyl-o-cresol); 2,6-di-tert-butylphenol; 6-(4-hydroxyphenoxy)-2,4-bis(n-octyl-thio)-1,3,5 triazine; di-n-octadecyl 3,5-di-tert-butyl-4-hydroxy-benzylphosphonate; 2-(n-octylthio) ethyl 3,5-di-tert-butyl-4-hydroxy-benzoate; and sorbitol [hex 3-(3,5-di-tert-butyl-4-hydroxyphenyl)-propionate.].

The hot-melt adhesive composition is prepared for use by blending the A-B-A block copolymer with the primary tackifying resin, the secondary tackifying resin or plasticizing oil, and stabilizer, in any order or sequence, or these materials can be added together simultaneously to form the adhesive composition. In commercial practice it would be expected that the primary tackifying resin and copolymer, with or without the simultaneous addition of the secondary tackifying resin or plasticizing oil, and stabilizer, would be blended together at sufficiently elevated temperature to form a fluid melt. For example, the copolymer can be blended with the solid compatible primary tackifying resin at temperatures ranging from about 130° C. to about 200° C., preferably at from about 150° C. to about 180° C., to form a fluid melt. The secondary liquid tackifying resin, or plasticizing oil, and stabilizer, can then be added to the melt. Alternatively, the fluid melt can be prepared with all components of the adhesive composition present ab initio.

The following non-limiting examples, and comparative data, bring out the more salient features of the invention. All parts are given in terms of weight units except as may otherwise be indicated.

In conducting the following tests the composition and properties of the neat A-B-A block copolymers which were prepared for making the adhesive compositions were determined by techniques "a," "b" and "c". In evaluating the performance characteristics of the adhesive compositions produced from the A-B-A block copolymers test procedures "d" through "h" were employed, to wit:

a. Styrene content-of the experimental A-B-A block copolymers was determined from the proton nmr spectra. Samples were dissolved in a mixture of deuterated tetrachlroethane/tetrachloroethylene and analyzed on a Bruker 90 MHz spectrometer. Styrene content was calculated from the spectra by the method of V. D. Mochel, *Rubber Chem. and Tech.*, 40, 1200 (1967).

b. Molecular Weight—of the experimental A-B-A block copolymers was determined by GPC, using the method described by J. R. Runyon, et al, *J. Polym. Sci.* 13, 2359 (1969).

c. Melt Flow Rate (MFR)—of the experimental A-B-A copolymers was determined according to ASTM method D-1238-82, using condition "G" (200° C., 5 Kg weight).

d. Adhesive Melt Viscosity (ASTM D-3236)—Melt viscosities were measured at a temperature of 130° C., using a Brookfield Thermosel viscometer. Low adhesive viscosities are a necessity for processing in multiline, spray, and fiberization equipment. In addition, the viscosity must be low at relatively low processing temperatures in order to avoid distortion of the polyolefin backing when hot adhesive is applied.

e. Shear Adhesion Failure Temperature (SAFT)—is a measure of the ability of the bond to withstand an elevated temperature rising at 10° F./15 min., under a constant force which pulls the bond in the shear mode. Bonds 1 inch by 1 inch were formed of adhesive, on a Mylar (polyester) backing, to a stainless steel panel, using a 4.5 lb. rubber roller. The panel was suspended vertically in an oven at 32° C., and allowed to come to equilibrium. A 1 kg weight was suspended from the free end of the adhesive tape, and the temperature was raised at 10° F./15 min. The temperature at which the tape and weight fell from the panel was recorded. SAFT was reported as the average of three such determinations. Adhesives possessing high failure temperatures are essential for the assembly of disposable articles, which are often subjected to very high temperatures during storage and shipping. In addition, these articles are used (worn) at body temperature.

f. Shear Holding Power (Static Time to Failure Bond Test)—The cohesive strength of the adhesives was determined according to the general procedures outlined in PSTC-7 and ASTM D-3654. A 1 inch by 0.5 inch bond was applied to a stainless steel panel with a 4.5 lb rubber roller. The plate was suspended vertically and allowed to equilibrate at 35° C. A 1 Kg weight was suspended from the free end of the tape. The time at which the tape and weight fell from the panel was recorded. The shear hold (in min) was reported as the average of four such determinations. Long failure times are desirable, since they indicate strong bonds, which are essential in certain areas of the disposable constructions, which are subjected to considerable stress during use.

g. 180 Degree Peel Adhesion—of the adhesives was determined according to the procedures outlined in PSTC-1 of the Pressure Sensitive Tape Council. A 1 inch by 6 inch strip of the adhesive tape (2 mil Mylar backing) was applied to a stainless steel panel with a 4.5 lb. rubber roller. The tape and panel were conditioned 24 hrs. under ASTM conditions of temperature and humidity prior to testing. The tape was then peeled back over itself at 180° in a tensile tester at a constant crosshead speed of 12 in/min. The average force required to peel the tape from the panel was recorded. The 180 peel (lb/in) was reported as the average of three such determinations.

h. Loop Tack—is that property of a pressure sensitive adhesive, which causes it to adhere to a surface instantly using no external pressure to secure a thorough bond. Loop tack is measured as the force resisting peeling of a tape at 90° from a standard surface upon which it has been applied under no other pressure than the weight of the tape itself. Loop tack was measured using a tensometer with a crosshead speed of 20 in/min. The tape contact area was 1 inch by 1 inch. The loop tack (lb/in) was reported as the average of three determinations. (Modified version of PSTC-5)

EXAMPLE 1

To a 2.6 liter autoclave were charged 1900 ml of cyclohexane and 88.1 gm of styrene monomer. The mixture was heated to 60° C. and 3.7 ml of a 1.4 molar solution of sec-butyllithium initiator in cyclohexane was added. After 40 minutes, when analysis of the reaction mixture indicated that polymerization of the styrene monomer was complete, the reaction temperature was reduced to 50° C., and 116.7 gm of isoprene was added. After 45 minutes, no unreacted isoprene was detected. The living styrene-isoprene diblock polymer was then coupled to form a styrene-isoprene-styrene triblock polymer by adding 32.0 ml of 0.12M 1,2-dibromoethane in cyclohexane over a period of 11 minutes. Analysis of the product by gel-permeation chromatography (GPC) indicated that the triblock polymer had a peak molecular weight of 76,800, and contained approximately 12% residual diblock. From the proton NMR spectrum of the product, it was determined that it contained 41.7 wt. % styrene. The solvent was removed from the polymer solution under vacuum at 90° C.

EXAMPLE 2

Using a procedure essentially identical to that of Example 1, 94.3 gm of styrene monomer was polymerized using 4.2 ml of 1.4 molar sec-butyllithium solution, followed by addition of 110.7 gm of isoprene. The resulting living polymer was then coupled by addition of 36.6 ml of 0.12 molar 1,2-dibromoethane. Analysis of the product, via the means described by reference to Example 1, shows that the triblock polymer had a peak molecular weight of 76,500, and that it was constituted of 44.8 wt. % styrene.

EXAMPLE 3

Using a procedure essentially identical to that of Example 1, 81.8 gm of styrene monomer was polymerized using 4.2 ml of 1.4 molar sec-butyllithium solution, followed by addition of 122.7 gm of isoprene. The resulting living polymer was then coupled by addition of 36.5 ml of 0.12 molar 1,2-dibromoethane. This product triblock polymer was found to have a peak molecular weight of 76,500, and was constituted of 38.6 wt. % styrene.

The pertinent properties of the block copolymers produced as described by Examples 1 through 3 are given in the Table below, particular reference being made to Columns 1 through 6 of the Table.

The following tabulates the amounts of the cyclohexane solvent, the initiator, the styrene monomer, the isoprene monomer, and dibromoethane employed in the preparation of additional polystyrenepolyisoprene-polystyrene (SIS) block copolymers, for comparative purposes, wherein one or more of the properties fall outside that required to produce a satisfactory adhesive, i.e., the average molecular weight required for the polystyrene end blocks, the polyisoprene mid block, overall molecular weight, or the wt. % styrene.

| Demonstration | 4 | 5 | 6 | 7 |
|---|---|---|---|---|
| Milliliters 1.4 M/L sec-butyllithium | 2.6 | 3.6 | 4.9 | 2.9 |
| Grams of Styrene Monomer | 44.8 | 55.0 | 65.3 | 55.0 |
| Grams of Isoprene Monomer | 158.7 | 148.7 | 138.7 | 148.7 |
| Milliliters 0.12 M/L dibromoethane | 23.1 | 32.9 | 44.0 | 25.5 |

The pertinent properties of SIS block copolymers produced by Demonstrations 4 through 7 are given in the Table below, particular reference being made to Columns 1 through 6 of the Table.

For comparative purposes also, two additional block copolymers of the polystyrene-polybutadienepolystyrene (S-B-S) type were prepared in generally similar manner except that in these instances (Demonstrations 8 and 9, respectively) accurately measured amounts of 1,3-butadiene was used in place of the isoprene in the preparation procedure.

The following tabulates the amounts of cyclohexane solvent, the initiator, the styrene and butadiene monomers, respectively, and dibromoethane employed in the preparation of the rubbers used in Demonstrations 8 and 9, respectively.

| Demonstration | 8 | 9 |
|---|---|---|
| Kg Cyclohexane Solvent | 12.6 | 11.8 |
| Milliliters 0.295 M/L sec-butyllithium | 228.2 | 314.2 |
| Grams of Styrene Monomer | 791.8 | 1090.0 |
| Grams of Butadiene Monomer | 1093.4 | 1505.2 |
| Milliliters 1.16 M/L | 43.5 | 59.9 |

| -continued | | |
|---|---|---|
| Demonstration | 8 | 9 |
| dibromoethane | | |

The pertinent properties of the SBS block copolymers produced by Demonstrations 8 and 9 are given in the Table below, specific reference being made to Columns 1 through 6 of the Table.

Additionally, for comparative purposes, several S-I-S block copolymers and an S-B-S block copolymer were obtained from commercial sources. Demonstrations 10-12 thus describe adhesive compositions formed from S-I-S block copolymer produced by Shell Chemical Company (Demonstrations 10 and 11) and Enichem Americas, Inc. (Demonstration 12), respectively. Demonstration 13 describes an adhesive composition formed from S-B-S block copolymer produced by Firestone Tire and Rubber Company.

Adhesive compositions were prepared by combining 100 parts of the block copolymer, 220 parts of ECR-149B (an aromatic modified aliphatic hydrocarbon tackifier resin, available from Exxon Chemical), 80 parts of Tufflo 6056 (a plasticizer oil available from Lyondell Petroleum Company), and 3 parts of Irganox 1010 (a stabilizer available from Ciba-Geigy), to produce a homogenous adhesive blend. The adhesive was coated on 2 mil thick Mylar (polyester) backing, to produce a 1.5 mil thick film, of adhesive.

The performance characteristics of the block copolymers are given in the Table, the adhesive formulations for the S-I-S "rubbers" of this invention, designated as Examples 1, 2 and 3, being set out for comparison with adhesive formulations prepared from S-I-S rubbers not of this invention (Demonstrations 4-7 and 10-12) and S-B-S rubbers (Demonstrations 8-9 and 13). Columns 1 and 2 of the Table identifies the specific test run and type of rubber tested. Columns 3-6 identifies the total wt. % styrene content of the rubber, the overall molecular weight ($\times 1000$) of a rubber, the molecular weight of the polyisoprene ($\times 1000$), and the molecular weight of the polystyrene ($\times 1000$), respectively. Columns 7-12 describe the results of the tests conducted on each of the adhesive formulations, viz. the adhesive viscosity, SAFT, holding power, peel and tack. It is clear that the adhesive compositions of this invention, i.e., Examples 1-3, exhibit superior SAFT (high temperature resistance), superior holding power (static time to failure), equivalent or lower viscosity, and equivalent peel and tack.

TABLE

| ADHESIVE FORMULATION: | PHR |
|---|---|
| Block Copolymer (RUBBER) | 100 |
| Primary Tackifier (ECR 149B) | 220 |
| Plasticizer Oil (TUFFLO 6056) | 80 |
| Stabilizer (IRGANOX 1010) | 3 |

| RUBBER | TYPE | WT % STYRENE | OVERALL MW/1000 | POLY-ISOPRENE MW/1000 | POLY-STYRENE MW/1000 | ADHES. VISC. 130 C. (CPS) | SAFT (C.) | 35 C. HOLD (MIN) | 180 PEEL SS (LB/IN) | 180 PEEL PE (LB/IN) | LOOP TACK SS (LB/IN) |
|---|---|---|---|---|---|---|---|---|---|---|---|
| EXAMPLE 1 | SIS | 41.7 | 76.8 | 44.8 | 16.0 | 5,300 | 72.7 | >3900 | 4.5 | 3.2 | 6.6 |
| EXAMPLE 2 | SIS | 44.8 | 76.5 | 42.2 | 17.1 | 6,800 | 76.5 | >3900 | 5.2 | 3.3 | 6.9 |
| EXAMPLE 3 | SIS | 38.6 | 76.5 | 47.0 | 14.8 | 5,400 | 70.1 | >3900 | 5.3 | 3.1 | 6.9 |
| DEMONSTRATION 4 | SIS | 24.7 | 120.3 | 90.6 | 14.9 | 17,200 | 65.0 | 1296 | 5.3 | — | 6.5 |
| DEMONSTRATION 5 | SIS | 27.1 | 86.4 | 63.0 | 11.7 | 4,800 | 61.0 | 405 | 4.6 | — | 6.2 |
| DEMONSTRATION 6 | SIS | 35.2 | 59.9 | 38.8 | 10.5 | 2,488 | 55.0 | 424 | — | — | — |
| DEMONSTRATION 7 | SIS | 28.8 | 121.9 | 86.8 | 17.6 | 32,500 | 77.7 | >3900 | — | — | — |
| DEMONSTRATION 8 | SBS | 42.0 | 61.3 | — | 12.9 | 10,600 | 64.0 | 1711 | 3.8 | — | 6.7 |
| DEMONSTRATION 9 | SBS | 42.0 | 66.0 | — | 13.9 | 9,000 | 66.0 | >3900 | 4.2 | — | 6.7 |
| DEMONSTRATION 10 (KRATON D1107) | SIS | 14.5 | 150.0 | 128.3 | 10.9 | 26,800 | 47.0 | 80 | 5.3 | 2.6 | 5.8 |
| DEMONSTRATION 11 (KRATON D1111) | SIS | 22.8 | 143.0 | 110.4 | 16.3 | 35,500 | 71.9 | 2889 | 6.6 | 2.9 | 6.7 |
| DEMONSTRATION 12 (EUROPRENE SOL T 193 B) | SIS | 24.2 | 109.0 | 82.6 | 13.2 | 12,100 | 64.1 | 741 | 5.5 | 2.9 | 6.5 |
| DEMONSTRATION 13 (STEREON 840 A) | SBS | 42.3 | 78.4 | — | — | 14,700 | 59.0 | 556 | 4.3 | 2.7 | 6.5 |

Note 1:
"KRATON" is a trademark of Shell Chemical Company
Note 2:
"EUROPRENE" is a trademark of Enichem Americas, Inc.
Note 3:
"STEREON" is a trademark of Firestone Tire And Rubber Company Continuing reference to the Table, Examples 1, 2 and 3 show the performance of adhesive compositions prepared from S-I-S block polymers whose % styrene, overall molecular weight, polyisoprene molecular weight, and polystyrene molecular weight are all within the preferred ranges of the S-I-S block copolymer required for the practice of this invention. It is required that all four of these parameters fall within the ranges expressed in order to obtain this superior adhesive performance. Demonstrations 4 through 7 represent adhesive compositions prepared from S-I-S block copolymers wherein one or more of the requisite parameters—viz. % styrene, overall molecular weight, polyisoprene molecular weight and polystyrene molecular weight—fall outside those requirements which are necessary to obtain superior hotmelt adhesives. The same is true of the adhesive compositions prepared from commercially available S-I-S block copolymers as represented by Demonstrations 10 (Kraton D 1107), 11 (Kraton D 1111), and 12 (Europrene SOL T 193 B), all of which were prepared from S-I-S block copolymers having one or more of the four parameters which fall outside of the requisite ranges. As shown by the Table, the adhesive compositions of Examples 1, 2 and 3 clearly exhibit the best combination of low adhesive viscosity, high SAFT, high 35° C. Hold, and good peel and tack to stainless steel and polyethylene.

The performance of the adhesive compositions prepared from S-I-S block copolymers, as illustrated by reference to Examples 1, 2 and 3, are also shown to be superior to those prepared from S-B-S block copolymers (Demonstrations 8, 9 and 13). This is surprising, because Stereon 840 A (Demonstration 13) has been held out as a S-B-S block copolymer of choice for the production of hot-melt adhesives, and the performance of adhesive compositions prepared from this particular S-B-S block copolymer has been exemplified as superior to adhesive compositions prepared from earlier S-I-S block copolymers. (Reference is made to U.S. Pat. No. 4,526,577). The performance of adhesive compositions made from Stereon 840 A as contrasted with the adhesive compositions of this invention, as shown by Examples 1, 2 and 3, however, is poor. Relative to an adhesive composition prepared from Stereon 840 A, adhesive compositions made form S-I-S block copolymers pursuant to the practice of this invention have lower viscosity, much higher SAFT, much longer shear holding times at 35° C., and better 180° Peel to polyethylene. Moreover, the adhesive compositions of this invention, as exemplified by Examples 1, 2 and 3, are also shown to be superior to an adhesive composition prepared from two specially prepared S-B-S block copolymers (Demonstrations 8 and 9).

An adhesive composition useful for magazine or book binding can also be formed from the hot-melt adhesive composition of this invention by the further addition to the hot-melt adhesive composition of up to about 5 percent, preferably from about 0.5 to about 5 percent, based on the weight of the hot-melt adhesive composition, of a hydrocarbon or petroleum derived wax. Exemplary petroleum derived waxes are, e.g., paraffin and microcrystalline waxes having melting points within a range of from about 55° C. to about 110° C., as well as low molecular weight polyethylene and Fischer-Tropsch waxes.

It is apparent that various modifications and changes can be made without departing the spirit and scope of the invention.

Having described the invention, what is claimed is:

1. A disposable article comprising a polyethylene or polypropylene substrate bonded to a tissue, non-woven fabric or absorbent fluff by use of a hot-melt adhesive composition which comprises:

from about 15 percent to about 35 percent, based on the weight of the hot-melt adhesive composition, of an A-B-A block copolymer wherein the B component is polyisoprene having an average molecular weight ranging from about 30,000 to about 70,000, the A component is polystyrene having an average molecular weight ranging from about 12,000 to about 20,000, the overall molecular weight of the block copolymer ranges from about 60,000 to about 110,000, and wherein the A component is present in an amount of at least 27 parts to about 50 parts per 100 parts by weight of the block copolymer, from about 45 percent to about 70 percent of a compatible primary tackifying resin, based on the weight of the hot-melt adhesive composition, from 0 percent to about 30 percent of a plasticizing oil or secondary tackifying resin, based on the weight of the hot melt adhesive composition, and from about 0.1 percent to about 2 percent of a stabilizer, based on the weight of the hot melt adhesive composition.

2. The article of manufacture according to claim 1 wherein the hot-melt adhesive composition contains from about 20 percent to about 30 percent of the A-B-A block copolymer.

3. The article of manufacture according to claim 1 wherein the hot-melt adhesive composition contains from about 50 percent to about 60 percent of the compatible primary tackifying resin.

4. The article of manufacture according to claim 1 wherein the hot melt adhesive composition contains from about 5 percent to about 20 percent of the plasticizing oil or secondary tackifying resin.

5. The article of manufacture according to claim 1 wherein the hot melt adhesive composition contains from about 0.5 percent to about 1.5 percent of the stabilizer.

6. The article of manufacture according to claim 1 wherein the average molecular weight of the B component of the A-B-A block copolymer ranges from about 35,000 to about 60,000, the average molecular weight of the A component ranges from about 14,000 to about 19,000, the overall molecular weight of the copolymer ranges from about 70,000 to about 95,000, and wherein the A component is present in amount ranging from about 35 parts to about 45 parts per 100 parts by weight of the copolymer.

7. The article of manufacture according to claim 1 wherein the primary tackifying resin is any compatible resin or mixture thereof selected from the group consisting of (1) natural and modified rosins; (2) glycerol and pentaerythritol esters of natural and modified rosins; (3) copolymers and terpolymers of natured terpenes; (4) polyterpene resins having a softening point, as determined by ASTM method E28-58T, of from about 80° to 150° C.; (5) phenolic modified terpene resins and hydrogenated derivatives thereof; (6) aliphatic petroleum hydrocarbon resins having a Ball and Ring softening point of from about 70° to 135° C.; (7) aromatic petroleum hydrocarbon resins, and mixed aromatic and aliphatic paraffin hydrocarbon resins, and the hydrogenated derivatives thereof; (8) aromatic modified alicyclic petroleum hydrocarbon resins and the hydrogenated derivities thereof; and (9) alicyclic petroleum hydrocarbon resins and the hydrogenated derivatives thereof.

8. The article of manufacture according to claim 1 wherein the disposable article is selected from the group consisting of diapers, sanitary napkins and bed pads.

9. The article of manufacture according to claim 1 wherein the adhesive component of the disposable article is applied as a discontinuous phase.

10. The article of manufacture according to claim 1 wherein the disposable article is of multi-line construction.

11. The article of manufacture according to claim 10 wherein the adhesive component used in forming the disposable article is applied as fine parallel longitudinal strips or as a multi-dot pattern of adhesive droplets.

12. The article of manufacture according to claim 1 wherein the A-B-A block copolymer is of one of the following formulae:
  (i) B—(AB)$_n$ wherein n is equal to or greater than 2;
  (ii) A—(BA)$_n$ wherein n is equal to or greater than 1; and
  (iii) (AB)$_n$ wherein n is equal to or greater than 2.

13. The article of manufacture according to claim 1 wherein the average molecular weight of the polystyrene ranges from about 14,000 to about 19,000.

14. The article of manufacture according to claim 1 wherein the compatible primary tackifying resin includes glycerol and pentaerythritol esters of natural or modified resins.

15. The article of manufacture according to claim 14 wherein the hot melt adhesive composition comprises from about 5 to about 20 percent of a plasticizing oil.

16. The article of manufacture according to claim 15 wherein the plasticizing oil is a petroleum derived oil.

17. The article of manufacture according to claim 15 wherein the plasticizing oil are oligomers of polypropylene, polybutene, hydrogenated polyisoprene, hydrogenated polybutadiene, polypiperylene and copolymers of piperylene and isoprene having an average molecular weight between about 350 and about 10,000, vegetable and animal oils including glycerol esters of fatty acid and polymerization products thereof.

18. A disposable article comprising a polyethylene or polypropylene substrate bonded to a moisture absorbent fabric or fluff by a hot melt adhesive comprising from about 15 to about 35 percent by weight of a styrene-isoprene-styrene block copolymer containing from 27 parts to about 50 parts per 100 parts by weight of the block copolymer of polystyrene and further wherein
  the average molecular weight of the polystyrene block is from about 12,000 to about 20,000;
  the average molecular weight of the polyisoprene block is from about 30,000 to about 70,000; and
  the overall molecular weight of the block copolymer being between from about 60,000 to about 110,000, said adhesive further a comprising a compatible primary tackifying resin and a stabilizer.

19. The disposable article according to claim 18 wherein the hot melt adhesive further comprises from about 45 to about 75 percent by weight of a compatible tackifying resin and from about 5 to about 30 percent by weight of a plasticizing oil.

20. The disposable article according to claim 19 wherein the hot melt adhesive further comprises between about 0.1 to about 2 percent by weight of a stabilizer.

21. The disposable article according to claim 20 wherein the tackifying resin is a single resin or mixture thereof selected from the group consisting of natural and modified rosins, glycerol and pentaerythritol esters of natural and modified rosins, copolymers and terpolymers of natured terpenes, polyterpene resins, phenolic modified terpene resins, aliphatic petroleum hydrocarbon resins and the hydrogenated derivatives thereof, aromatic petroleum hydrocarbon resins and the hydrogenated derivatives thereof and mixed aromatic and aliphatic paraffin hydrocarbon resins and the hydrogenated derivatives thereof.

22. The disposable article according to claim 21 wherein the natural and modified resins include gum rosin, wood rosin, tall oil rosin, distilled rosin, hydrogenated rosin, dimerized rosin and polymerized rosin.

23. The disposable article according to claim 20 wherein the tackifying resin is a styrenated terpene.

24. The disposable article according to claim 20 wherein the hot melt adhesive further comprises up to about 5 percent by weight of a hydrocarbon or petroleum wax.

25. The disposable article according to claim 18 wherein the moisture absorbent fabric or fluff is a nonwoven fabric.

26. The disposable article according to claim 18 wherein the hot melt adhesive is applied as a continuous or discontinuous film.

27. The disposable article according to claim 18 wherein the disposable article is of multi-line construction.

28. The disposable article according to claim 27 wherein the hot melt adhesive is applied as fine parallel longitudinal strips or as a multi-dot pattern of adhesive droplets.

29. The disposable article according to claim 18 wherein the disposable article is selected from diapers, sanitary napkins and bed pads.

* * * * *